United States Patent
Schneider et al.

(10) Patent No.: US 6,683,182 B2
(45) Date of Patent: Jan. 27, 2004

(54) METHOD FOR PRODUCING LAMOTRIGINE FROM α-OXO-2,3-DICHLOROPHENYL ACETAMIDINO-AMINOGUANIDINO HYDRAZONE BY RING CLOSURE REACTION

(75) Inventors: Géza Schneider, Budapest (HU); Csaba Lehel Gegö, Budapest (HU); Levente Ondi, Budapest (HU); Attila Gergely Máté, Budapest (HU); Ferenc Lukács, Kistarcsa (HU); Miklós Nyerges, Budapest (HU); Sándor Garaczi, Budapest (HU)

(73) Assignees: Helm AG (DE); CF PharmaGyogyszergyarto Kft. (HU)

( * ) Notice: Subject to any disclaimer, the term of this patent is extended or adjusted under 35 U.S.C. 154(b) by 0 days.

(21) Appl. No.: 10/343,225
(22) PCT Filed: Jul. 4, 2002
(86) PCT No.: PCT/EP02/07433
§ 371 (c)(1), (2), (4) Date: May 15, 2003
(87) PCT Pub. No.: WO03/008393

PCT Pub. Date: Jan. 30, 2003

(65) Prior Publication Data
US 2003/0191310 A1 Oct. 9, 2003

(30) Foreign Application Priority Data
Jul. 17, 2001 (DE) .......................................... 101 34 980

(51) Int. Cl.$^7$ ............................................. C07D 253/07
(52) U.S. Cl. ....................................................... 544/182
(58) Field of Search .......................................... 544/182

(56) References Cited
FOREIGN PATENT DOCUMENTS

| EP | 0 963 980 | 12/1999 |
|---|---|---|
| WO | WO96/20934 | 7/1996 |
| WO | WO00/35888 | 6/2000 |
| WO | WO01/49669 | 7/2001 |

*Primary Examiner*—John M. Ford
(74) *Attorney, Agent, or Firm*—Shanks & Herbert

(57) ABSTRACT

The present invention relates to a method for producing 3,5-diamino-6-(2,3-dichlorophenyl)-1,2,4-triazine (lamotrigine) by cyclization reaction from α-oxo-2,3-dichlorophenylacetamidino-aminoguanidino-hydrazone.

5 Claims, No Drawings

METHOD FOR PRODUCING LAMOTRIGINE FROM α-OXO-2,3-DICHLOROPHENYL ACETAMIDINO-AMINOGUANIDINO HYDRAZONE BY RING CLOSURE REACTION

The present invention relates to a method for producing Lamotrigine as well as intermediate products used in the method.

Lamotrigine (3,5-diamino-6-(2,3-dichlorophenyl)-1,2,4-triazine) has the formula I

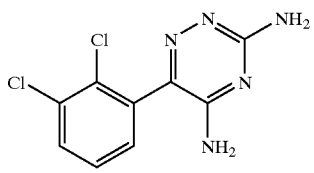

This compound, disclosed for example in European patent publication EP-A-0 021 121, is suitable for treating disorders of the central nervous system, in particular epilepsy, and since 1990 has been used in spasmolytic medications in numerous countries.

To date a variety of methods for producing Lamotrigine have been disclosed. Common to the methods disclosed in EP-A-0 021 121, EP-A-0 247 892, EP-A-0 963 980 and WO 00/35888 is the fact that cyclization of 2-(2,3-dichlorophenyl)-2-(guanidinylimino)acetronitrile (formula II) represents the final synthesis step.

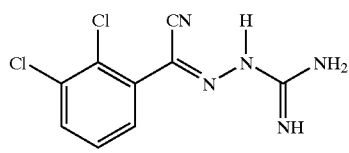

The compound of formula II required for the cyclization reaction may be obtained in a variety of ways. The following reaction model illustrates the reaction sequence disclosed in EP-A-0 963 980:

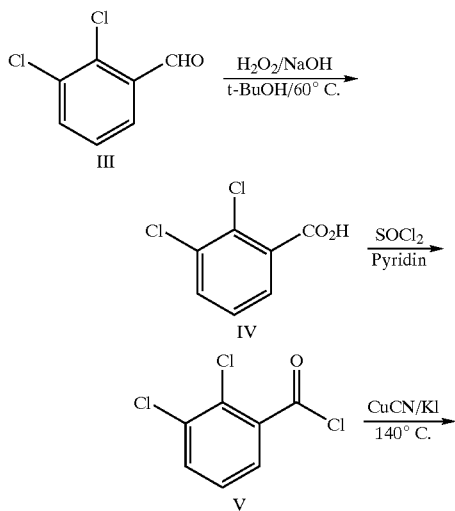

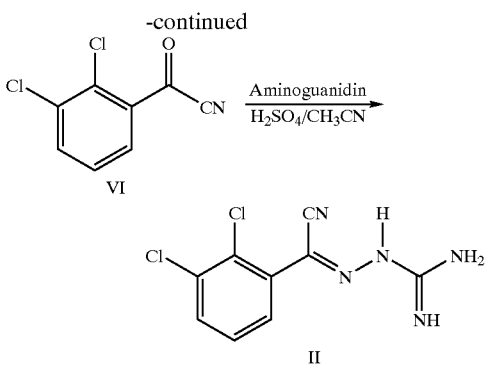

The methods disclosed in the aforementioned patent applications for producing lamotrigine by way of a cyclization reaction with a compound of formula II deviate in individual steps from the reaction sequence illustrated above. Common to all of them, however, is that the compound of formula (II) is obtained by reacting 2,3-dichlorobenzoyl cyanide (formula VI) with aminoguanidine. In accordance with the aforementioned patent applications 2,3-dichlorobenzoyl cyanide is produced by reaction with copper cyanide from 2,3-dichlorobenzoyl chloride (formula V).

A drawback of the above-described method of synthesis for producing lamotrigine is that the 2,3-dichlorobenzoyl cyanide (formula VI) required for synthesizing the compound of formula II can only be obtained in a form that is oily and difficult to purify, in addition to which the compound is unstable and prone to dimerization Further, the copper cyanide needed for synthesis of the 2,3-dichlorobenzoyl cyanide (formula VI) is relatively costly.

Moreover, during synthesis of the 2,3-dichlorobenzoyl cyanide (formula VI) a contaminant in the form of 2,3-dichlorobenzoe acid anhydride is produced. According to EP-A-0 963 980 this anhydride can be reacted with lamotrigine in the subsequent reaction sequence to form a compound of formula VII, which is an undesirable impurity.

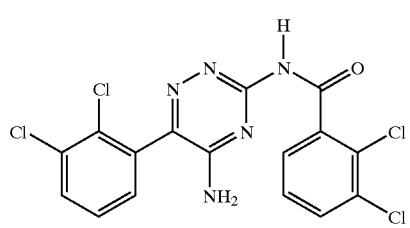

EP-A-0 963 980 also cites as an additional undesirable impurity a compound of formula VIII

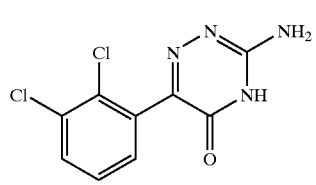

which is produced by hydrolysis of lamotrigine under basic conditions. For this reason, several of the methods of synthesis disclosed in the above cited patent applications are further disadvantageous because the cyclization reaction of the compound of formula II is performed in a highly basic environment, such that the undesirable impurity VIII is able to form through hydrolysis even during lamotrigine synthesis.

An alternative method of lamotrigine synthesis is disclosed in WO 96/20934, in which the cyclization reaction is performed using a compound analogous to the compound of formula II, which analogous compound contains an acid amide group instead of the cyanide group. Such a cyclization reaction must be initiated photochemically, however, and this is invariably coupled with technical difficulties.

The WO 96/20935 patent publication discloses a method for producing lamotrigine from 6-(2,3-dichlorophenyl)-3-methylthio-5-chloro-1,2,4-triazine. In replicating this method HPLC was used to identify larger quantities of unknown by-products in addition to lamotrigine in the reaction mixture.

Hence, there exists a continuing need for methods by which to obtain lamotrigine industrially, as economically as possible and in purest possible form.

Thus, an object of the present invention was to provide a method for producing lamotrigine that eliminates the aforementioned drawbacks.

It was found unexpectedly that lamotrigine may be obtained in highly pure form in a cyclization reaction from an intermediate compound not heretofore described.

The present invention thus relates to a method for producing lamotrigine or a pharmaceutically acceptable salt thereof, in which a cyclization reaction is performed using a compound of formula XII

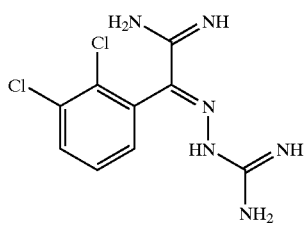

XII or a salt thereof, and optionally from which salt of the compound of formula 1 the free base is released and, if desirable, said free base is converted to a pharmaceutically acceptable salt.

As a result of the cyclization reaction according to the present invention with compound XII to lamotrigine, the latter is obtained in high yields and in especially pure form under mild conditions. In addition, the compound of formula XII is easily accessed using a simple method of synthesis and is readily purified by crystallization. Given the high purity of the reactant in the cyclization reaction according to the present invention, as compared to known reactions, it is possible to achieve an especially high purity level of the desired lamotrigine, a purity level required for pharmaceutical preparations, without the need for complex purification steps. In particular, there were no impurities of formulas VII and VIII cited in EP-A-0 963 980 detected in the lamotrigine produced according to the method of the present invention.

The cyclization reaction may be performed by heating under mild conditions, for example, at a temperature in the range of 100°–170° C., preferably 130°–170° C. It is preferable to perform the cyclization reaction in solution. Solvents suitable for the compound of formula XII are all organic solvents that have no adverse affect on the reaction, preferably dimethylsulfoxide or dimethylformamide. Especially preferred are solvents having a boiling point in the desired temperature range, such that the reaction may occur at the boiling temperature of the solvent under reflux. To adjust a desired boiling temperature it is feasible to also use solvent mixtures of, for example, dimethylsulfoxide or dimethylformamide and benzol, toluol or xylol.

The cyclization reaction should be performed to the exclusion of water or substantially to the exclusion of water.

The cyclization reaction may be performed with the free base of the compound of formula XII or with an acid addition salt of said compound. A preferred acid addition salt is dihydrochloride. When the cyclization reaction is performed using an acid addition salt, the product obtained is the acid addition salt of lamotrigine. In such case, the free lamotrigine base may, if desired, be obtained in nearly quantitative yield in a manner known to one skilled in the art, e.g. using aqueous sodium hydroxide solution in dimethylformamide.

The time required for the cyclization reaction is a function of the process conditions and in particular the temperature at which the reaction is performed. The time can range, for example, from 1–24 hours. An optimal time period is easily determined by one skilled in the art.

In a preferred embodiment of the method according to the present invention, the compound of formula XII required for the cyclization reaction is obtained by reacting a compound of formula XI

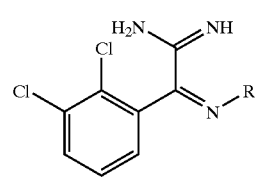

XI in which R is a substituted or unsubstituted straight- or branched-chained, or cyclical alkyl-, aryl- or aralkyl-residue, or a salt thereof, with aminoguanidine or a salt thereof.

In the compound of formula XI, R may be a straight-chained, branched or cyclical alkyl residue, preferably $C_{1-20}$—, in particular $C_{1-10}$-alkyl residue, such as for example methyl, ethyl, n-propyl, iso-propyl, n-butyl, iso-butyl, tert-butyl or cyclohexyl. Preferred alkyl residues for R are phenyl and naphthyl, in particular phenyl. Preferred aralkyl residues for R are aryl-$C_{1-5}$-alkyl residues, wherein aryl is defined as above, and in particular benzyl.

The aforementioned alkyl-, aryl-, and aralkyl-residues may optionally bear one or more, in particular 1 or 2 substitutents such as for example halogen, hydroxy, $C_{1-8}$-alkoxy or nitro. The aryl- and aralkyl-residues may be substituted in addition to, or alternatively, with $C_{1-6}$-alkyl.

R is preferably phenyl.

The compound of formula XII is produced by reacting the compound of formula XI with aminoguanidine or a salt thereof, preferably with aminoguanidine-hydrochloride. The reaction takes place preferably in the presence of a potent mineral acid, e.g. hydrochloric acid. A suitable solvent is in principal any solvent that does not adversely affect the reaction. It is preferable to perform the reaction in water or in an alcohol. The reaction temperature is not otherwise restricted and may range, for example, from between 40°–120° C.

When the compound of formula XI is reacted in the presence of hydrochloric acid, the dihydrochloride of the compound of formula XII is obtained. This may then either be directly converted by cyclization reaction to lamotrigine-hydrochloride, as described above, or, if desired, the free base of the compound of formula XII may be obtained prior thereto in a manner known to one skilled in the art, e.g. using aqueous sodium hydroxide solution.

In a particularly preferred embodiment of the method according to the present invention the compound of formula XI or a salt thereof is obtained by reacting a compound of formula X

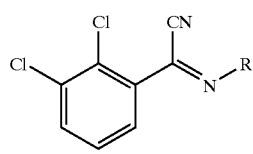

in which R is as defined above, first with an alcohol solution of a hydrohalic acid, then with NH₃. This reaction path is especially advantageous because the compound of formula X is surprisingly stable and is readily purified by crystallization. The prior art, analog compound of formula X, 2,3-dichlorobenzoyl cyanide, used in the synthesis of lamotrigine is an oily, unstable product difficult to purify and it contributes significantly to the contamination of the lamotrigine obtained through synthesis, whereas the compound of formula X is crystalline and stable, making it is easy to purify. For this reason the method according to the present invention makes it possible to produce even at this point in the synthesis path an especially pure lamotrigine, since already the intermediate stages themselves may be obtained in especially pure form. Moreover, it is possible to obtain the compound of formula X, as is further explained below, by reaction with sodium cyanide in lieu of copper cyanide used in the prior art for synthesizing 2,3-dichlorobenzoyl cyanide. Sodium cyanide is less expensive than copper cyanide, hence it is possible to synthesize lamotrigine using the method of the present invention in an overall highly economical and cost effective manner.

Conversion of the compound of formula X to the compound of formula XI proceeds in two steps, in which said compound is first reacted with an alcohol solution of a hydrohalic acid, preferably a methanol or ethanol hydrochloric acid solution, then with NH₃, e.g. by addition of ethanol saturated with ammoniac. Both reaction steps may be performed, for example, in a temperature range of between −30° and +10° C.

When the reaction of the compound of formula X is performed in the presence of hydrochloric acid, hydrochloride of the compound of formula XI is obtained. This product may, if needed, be used again in the method according to the present invention after purification, e.g. through re-crystallization, and without releasing the free base.

The α-iminonitriles of formula X are easily accessed, e.g. as described in German laid-open publication No. 2 221 771. However, in a preferred embodiment of the method according to the present invention, the compound of formula X is produced by reacting a nitrone of formula IX,

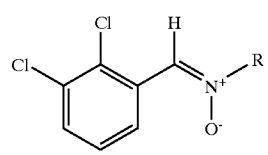

in which R is as defined above, with a cyanide. The advantage of this variation over and against the prior art method of producing lamotrigine is that cyanide in the form of sodium cyanide may be used, which compared to copper cyanide used in the prior art methods is less expensive and easier to handle.

The nitrone of formula IX may be reacted with cyanide, preferably sodium cyanide, for example in an aqueous buffer, for example a phosphate, acetate or tartrat buffer, in particular a phosphate buffer, at e.g. a pH-value in the range of 4–8. It is advantageous to use as a co-solvent a low alcohol, preferably methanol. The reaction may occur within a broad temperature range, e.g. from ambient temperature to about 80° C.

The nitrone of formula IX is obtained, for example, according to the method described by M. P. Grammaticakis in Bull. Soc. Chim. Fr. [1951], p. 971.

Further, the present invention relates to compounds of formulas IX, X XI and XII and salts thereof which occur as intermediate products in the method according to the present invention. Still further, the present invention relates to the use of compounds of formulas IX, X, XI and XII or salts thereof for producing lamotrigine.

Lamotrigine produced by the method according to the present invention is suitable for the manufacture of pharmaceutical compositions, in which in particular pharmaceutically acceptable salts of lamotrigine are used. Suitable pharmaceutically acceptable salts and suitable pharmaceutical compositions are described, for example, in EP-A-0 021 121, EP-A-0 247 892 and WO 96/20935.

The method according to the present invention is described below in greater detail with reference to but not limited to the following examples.

EXAMPLE 1

α-(phenylimino)-2,3-dichlorophenyl acetonitrile (X)

635 mMol of N-(2,3-dichlorophenylmethylene)anilin-N-oxide (IX) are dissolved in a 5.6l mixture (1:1) of an aqueous 0.5 molar solution of potassium dihydrogenphosphate and methanol adjusted to pH5. To this are added 65 g (1.3 Mol) of sodium cyanide in 200 ml water at approximately 50° C. During the reaction the pH balance is held constant between 8.0 and 8.5. After the reaction is complete (DC control), the reaction mixture is neutralized and cooled to 0° C. The separated yellow-brown crystals are then dissolved in methylene dichloride. The organic phase is washed in water, dried and evaporated under vacuum. The residue is recrystallized from a small amount of methanol.

| Yield: | 157 g |
|---|---|
| Purity: | 99.0% (HPLC) |
| Melting point: | 65°–67° C. |

The NMR spectroscopic data correspond to the chemical structure.

EXAMPLE 2

α-(phenylimino)-2,3-dichlorophenyl acetamidine-hydrochloride (XI-HCL)

151.2 g of α-(phenylimino)-2,3-dichlorophenyl acetonitrile (X) are introduced in an ethanol hydrochloric acid solution (made from 400 ml ethanol, 240 ml thionylchloride and 52 ml water) at −10° C. and stirred at that temperature for several hours. The reaction mixture is then combined at −10° C. with 6.5l ethanol saturated with ammoniac and stirred for 12 hours at room temperature. The reaction solution is then concentrated by evaporation and the product thereof precipitated out with the addition of water, filtered and dried. The product (XI-HCL) may be further purified through re-crystallization from acetone.

| Yield: | 166.7 g |
|---|---|
| Purity: | 99.7% (HPLC) |
| Melting point: | 263°–267° C. |

The NMR spectroscopic data correspond to the chemical structure.

EXAMPLE 3
α-oxo-2,3-dichlorophenylacetamidino-aminoguanidino-dihydrochloride (XII-2HCL) 82.5 g (250 Mmol) of α-phenyllimino-2,3-dichlorophenylacetamidine-hydrochloride (XI-HCL) are introduced after gas formation has subsided in a solution of 83.2 g (550 mMol) aminoguanidine-bicarbonate (purity: 90%) in 500 ml of 10 m hydrochloric acid and heated to reflux. An equal amount of α-phenyllimino-2,3-dichlorophenylacetamidine-hydrochloride (XI-HCL) is added again, and the reaction mixture is maintained at this temperature for several hours until the reaction is completed.

Upon completion the reaction is cooled to 0° C. and the precipitated product is filtered off and washed in ice water. The hygroscopic product may be substantially dried by maintaining it for a lengthier period of time in vacuum at a slightly elevated temperature.

| Yield: | 160.0 g (91.5%) g |
|---|---|
| Purity: | 99.0% (HPLC) |
| Melting point: | 218°–220° C. (decomposed) |

EXAMPLE 4
α-oxo-2,3-dichlorophenylacetamidino-aminoguanidino-hydrazone (XII)

The free base of the dihydrochloride (XII-2HCL) may be obtained by conventional means using aqueous sodium hydroxide solution.
Melting point: 2000–203° C.

EXAMPLE 5
Lamotrigine-hydrochloride (L-HCL)

20.76 g of α-oxo-2,3-dichlorophenylacetamidino-aminoguanidino-hydrazone-dihydrochloride (XII-2HCL) (water content below 0.05%) are heated to reflux in dry dimethylformamide for approximately 20 hours. The residue obtained after extraction of the solvent is briefly heated to boiling with 200 ml isopropanol, then cooled to 20° C. The precipitated crystals are filtered off and re-crystallized from an aqueous isopropanol (volume ratio 1:1) and dried in vacuum at 80° C.

| Yield: | 10.6 g (60.5%) |
|---|---|
| Purity: | 99.5% (HPLC) |
| Melting point: | 233°–235° C. (decomposed) |

The free lamotrigine base may be obtained in nearly quantitative yield by conventional means by being released with aqueous sodium hydroxide solution in dimethylformamide.
Melting point: 216°–217° C.

EXAMPLE 6
Lamotrigine (1)

8.19 g of α-oxo-2,3-dichlorophenylacetamidino-aminoguanidino-hydrazone (XII) (max. water content 0.3%) are dissolved in 150 ml of dry dimethylformamide at 60° C. The solution is evaporated by around 20% under vacuum, after which the temperature is raised to reflux and maintained at this temperature for 1.5 hours. The reaction mixture is then concentrated by evaporation and cooled to room temperature, after which 6.7 g of the crude product are isolated, which for purification are re-crystallized from isopropanol.

| Yield: | 5.1 g (66.7%) |
|---|---|
| Purity: | 99.9% (HPLC) |
| Melting point: | 215.5°–216.5° C. (decomposed) |

What is claimed is:

1. Method for producing a compound of formula I

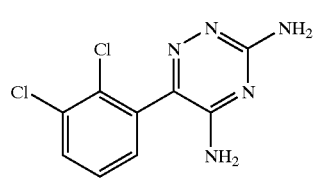

or a pharmaceutically acceptable salt thereof, in which a cyclization reaction is performed with a compound of formula XII

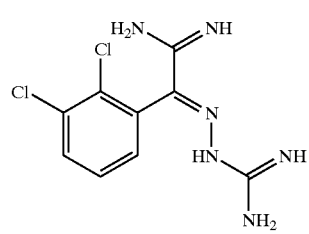

or a salt thereof and, optionally, from which salt of the compound of formula I thus obtained the free base is released and, if desired, said free base is converted to a pharmaceutically acceptable salt.

2. Method according to claim 1, in which the cyclization reaction is performed by heating.

3. Method according to claim 2, in which the cyclization reaction is performed at a temperature in the range of between 100° C. and 170° C.

4. Method according to claim 1, in which the cyclization reaction is performed using an acid addition salt, of the compound of formular XII.

5. Method according to claim 4, wherein the acid addition salt is the dihydrochloride of the compound of formular XII.

* * * * *